US 6,689,903 B2

(12) United States Patent
O'Meadhra et al.

(10) Patent No.: US 6,689,903 B2
(45) Date of Patent: Feb. 10, 2004

(54) CRYSTALLIZATION METHOD FOR PRODUCTION OF PURIFIED AROMATIC DICARBOXYLIC ACIDS

(75) Inventors: Ruairi Seosamh O'Meadhra, Kingsport, TN (US); Robert Lin, Kingsport, TN (US); Shane Kipley Kirk, Church Hill, TN (US); Brian David McMurray, Bristol, VA (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/159,394

(22) Filed: May 30, 2002

(65) Prior Publication Data
US 2002/0198405 A1 Dec. 26, 2002

Related U.S. Application Data
(60) Provisional application No. 60/295,669, filed on Jun. 4, 2001.

(51) Int. Cl.[7] .......................... C07C 51/42; C07C 57/34; C07C 51/16
(52) U.S. Cl. ........................ 562/486; 562/489; 562/414; 562/416
(58) Field of Search ................ 562/486, 489, 562/414, 416

(56) References Cited

U.S. PATENT DOCUMENTS

| 3,452,088 A | | 6/1969 | Olsen et al. | |
|---|---|---|---|---|
| 3,584,039 A | * | 6/1971 | Meyer | 562/416 |
| 3,799,976 A | * | 3/1974 | Nienburg et al. | 562/416 |
| 3,931,305 A | | 1/1976 | Fisher | |
| 4,467,111 A | * | 8/1984 | Puskas et al. | 562/487 |
| 4,500,732 A | | 2/1985 | Petty-Weeks et al. | |
| 5,110,984 A | * | 5/1992 | Janulis | 562/487 |
| 5,175,355 A | * | 12/1992 | Streich et al. | 562/485 |
| 5,567,842 A | | 10/1996 | Izumisawa et al. | |
| 5,583,254 A | | 12/1996 | Turner et al. | |
| 5,756,833 A | | 5/1998 | Rosen et al. | |

FOREIGN PATENT DOCUMENTS

| DE | 1925038 | 11/1970 |
|---|---|---|
| JP | 2001-288139 A | 10/2001 |

OTHER PUBLICATIONS

PCT International Search Report.
DE 1925038 (ABS) Standard Oil Company Nov. 26, 1970.
DE WPI Acc No.: 1968–73042P/196800.
WPI Acc No.: 1968–29536Q/196800.

* cited by examiner

Primary Examiner—Alan L. Rotman
Assistant Examiner—Taylor V. Oh
(74) Attorney, Agent, or Firm—Dennis V. Camen; Bernard J. Graves, Jr.

(57) ABSTRACT

Disclosed is a method for the recovery of crystalline terephthalic acid containing less than about 150 ppmw p-toluic acid by subjecting a solution of terephthalic acid containing minor amounts of p-toluic acid to crystallization in a crystallization zone comprising a plurality of series-connected crystallizers wherein the solution is subjected to rate-controlled evaporative cooling by sequential reduction in pressure and temperature to cause crystallization of terephthalic acid, wherein the pressure of the solution at the end of the crystallization zone is about ambient pressure or less. Solvent which is evaporated from the crystallizers is collected and condensed and the condensed solvent is returned to the crystallization zone at a point subsequent to the crystallizer from which it was obtained.

9 Claims, 1 Drawing Sheet

CRYSTALLIZATION METHOD FOR PRODUCTION OF PURIFIED AROMATIC DICARBOXYLIC ACIDS

CROSS REFERENCE TO RELATED APPLICATION

This application claims the benefit of U.S. Provisional Application Ser. No. 60/295,669 filed Jun. 4, 2001.

BACKGROUND OF THE INVENTION

Terephthalic acid (TPA) is one of the basic building blocks in the production of linear polyester resins used in the manufacture of polyester films, packaging materials and bottles. TPA used in the manufacture of such polyesters resins must meet certain minimum purity requirements. The purified condition of terephthalic acid refers primarily to the absence of significant concentrations of 4-carboxybenzaldehyde (4-CBA) and p-toluic acid that are present in significant quantities in the crude commercially-available grades of terephthalic acid. Both CBA and toluic acid are partial oxidation products formed in the manufacture of TPA by the catalytic oxidation of p-xylene. The purified form also refers to the absence of color bodies that impart a characteristic yellow hue to the crude material. The color bodies are aromatic compounds having the structures of benzils, fluorenones, and/or anthraquinones. 4-CBA and p-toluic acid are particularly detrimental to the polymerization process as they act as chain terminators during the condensation reaction between terephthalic acid and ethylene glycol in the production of poly(ethylene terephthalate) (PET).

To obtain purified terephthalic acid (PTA) from crude TPA, the 4-CBA and the color bodies are hydrogenated, the 4-CBA to p-toluic acid and the color bodies to compounds that are colorless solids. Typically, crude terephthalic acid dissolved in a solvent such as water is subjected to a liquid phase hydrogenation of the impurities in the presence of an immobilized or fixed bed catalyst. The 4-CBA is converted to p-toluic acid in high yields.

The hydrogenation process proceeds at elevated temperatures of between 250° C. and 280° C. using a partial pressure of hydrogen in the range 0.5 to 20 bars absolute-bara (0.05 to 2.0 Mpa). The concentration of the TPA in aqueous TPA solutions fed to the hydrogenation reactor typically is in the range of about 15 to 30 weight percent. The hydrogenated product stream normally is passed to a series of crystallization units in which purified terephthalic acid (PTA) is crystallized from solution in a crystalline form that can be readily filtered and dried.

The staged equilibrium crystallization technique is described in U.S. Pat. No. 3,452,088 which discloses the controlled evaporation or flashing of solvent by back-pressure regulation in multiple stages to control the rate at which the hydrogenation product stream is crystallized. U.S. Pat. No. 3,542,088 discloses that shock cooling of the post-hydrogenation stream to temperatures below 165° C. should be avoided since shock or sudden cooling promotes the co-precipitation of other impurities, particularly p-toluic acid, which contaminate the purified TPA product. This caution is repeated in more general terms in U.S. Pat. No. 3,931,305, which states that "Such contamination phenomenon is somewhat anomalous because, in spite of the fact that there is retained more than enough solvent water to prevent saturation or supersaturation with respect to p-toluic acid, p-toluic acid nevertheless comes out of solution." U.S. Pat. No. 3,452,088 suggests that the contamination phenomenon is in some way dependent on the rate of crystallization and the final temperature of crystallization and product separation and not solely on p-toluic acid concentration in the solution." U.S. Pat. No. 3,931,305 concludes that the primary factor determining p-toluic acid concentration in the final TPA product is the lowest temperature to which the post-hydrogenation solution is flashed. It is less a function of the rate at which it is cooled to this temperature. It was determined that a final filtration temperature of between 121 and 149° C. is desired to obtain a p-toluic acid concentration of less than 150 ppm in the final TPA product when the crude material has a concentration from 500 ppm to 6,000 ppm.

U.S. Pat. No. 3,931,305 discloses that in a system wherein TPA is crystallized in a train of series-connected crystallizers, the temperature dependent precipitation of TPA becomes critical below a temperature between 160 and 182° C. The '305 patent thus recommends that the majority of the TPA be crystallized before this threshold is reached to minimize contamination with p-toluic acid. More specifically, the '305 patent discloses the crystallization of 75–95% of the originally dissolved TPA in substantially equal portions in the first two crystallization zones at a temperature of 160 to 182° C. and thereafter crystallizing the remaining 5–25% of the originally dissolved TPA in decreasing incremental portions.

Another limitation on the recovery of TPA substantially free of p-toluic acid is set by the lowest processing temperature at which the TPA solids can be separated from the crystallization mother liquor. Based on the above-cited patent literature, this temperature is above the normal boiling temperature of the water solvent. Hence, any process for separating the TPA solids from the crystallization mother liquor must be conducted at superatmospheric pressures. Such a processing limitation requires the separation equipment to have a more robust construction than its atmospheric or near atmospheric pressure counterparts. Hence, from the standpoint of capital investment cost, use of atmospheric or near atmospheric pressure separation equipment is desirable.

SUMMARY OF THE INVENTION

The present invention provides a process for the recovery of purified TPA product from a hydrogenation product obtained by the hydrogenation of a solution of crude TPA using a sequence of series-connected crystallizers. The present invention provides a process for the recovery of crystalline terephthalic acid containing less than about 150 parts per million by weight (ppmw) p-toluic acid, based on the weight of the terephthalic acid, by the steps comprising:

(1) providing a solution containing about 10 to 35 weight percent dissolved terephthalic acid having dissolved therein about 150 to 1100 ppmw p-toluic acid, based on the weight of the terephthalic acid present, and having a temperature of about 260 to 320° C. at a pressure sufficient to maintain the solvent in the liquid phase;

(2) feeding the solution of step (1) to a crystallization zone comprising a plurality of series-connected crystallizers wherein the solution is subjected to rate-controlled evaporative cooling by sequential reduction in pressure and temperature to cause crystallization of terephthalic acid, wherein the pressure of the solution at the end of the crystallization zone is about ambient pressure or less;

(3) condensing solvent evaporated from the crystallizers and returning the condensed solvent to the crystallization zone at a point subsequent to the crystallizer from which it was obtained; and (4) recovering solid, crystalline terephthalic acid containing less than about 150 parts ppmw p-toluic acid, based on the weight of the terephthalic acid, by liquid-solid separation at ambient pressure.

According to our invention, solvent evaporated from at least one of the crystallizers constituting the crystallization zone is condensed and recycled to one of the subsequent crystallizer stages. The advantages provided by our novel process include the recovery of terephthalic acid in an improved crystalline form with less "fines", i.e., small crystals or particles of TPA, which can cause problems in the handling and conveying of the TPA. Another advantage is the product recovery at ambient or approximately ambient pressure.

To obtain the same recovery of TPA per stage as demonstrated in U.S. Pat. No. 3,931,305, the temperatures can be staged much closer to each other in the process of the present invention, thus allowing shock cooling of the post-hydrogenation stream to be minimized at the temperatures where most of the TPA is crystallized from solution. The corollary of this statement is also true: that at the temperatures demonstrated in U.S. Pat. No. 3,931,305 more of the TPA will crystallize from solution at the stated unit temperatures when the system is operated as described in this invention. For a given residence time and production rate, the volume of the crystallizers required by the process described herein is much smaller than the volume required by known process as the initial TPA concentration in solution is much higher while still targeting the same suspended solids content in the final product stream. The smaller volume that is required of the crystallizers results in a significant cost saving. The crystallization of TPA at higher temperatures is reported to cause less p-toluic acid to be co-crystallized with the TPA. This further contrasts the present process from the process and the critical temperature range described in U.S. Pat. No. 3,931,305.

Recycle of condensed solvent directly back into the crystallizer stage from which it evaporated, commonly known as total reflux, does not meet the requirements of the present invention since such a reflux stream is acting as an additional feed stream diluting the TPA laden feed stream. This increase in total feed material requires an enlargement of the vessel volume to maintain a given residence time which may not be desired.

BRIEF DESCRIPTION OF THE DRAWINGS

The accompanying FIGURE is a process flow diagram illustrating a process for the recovery of crystalline terephthalic acid embodying the principles of the present invention. While the present invention is susceptible to embodiment in various forms, there is shown in the Figure and hereinafter described in detail preferred embodiments of the invention. However, the present disclosure is to be considered as an exemplification of the invention without limitation to the specific embodiments illustrated.

DETAILED DESCRIPTION

Figure 1:
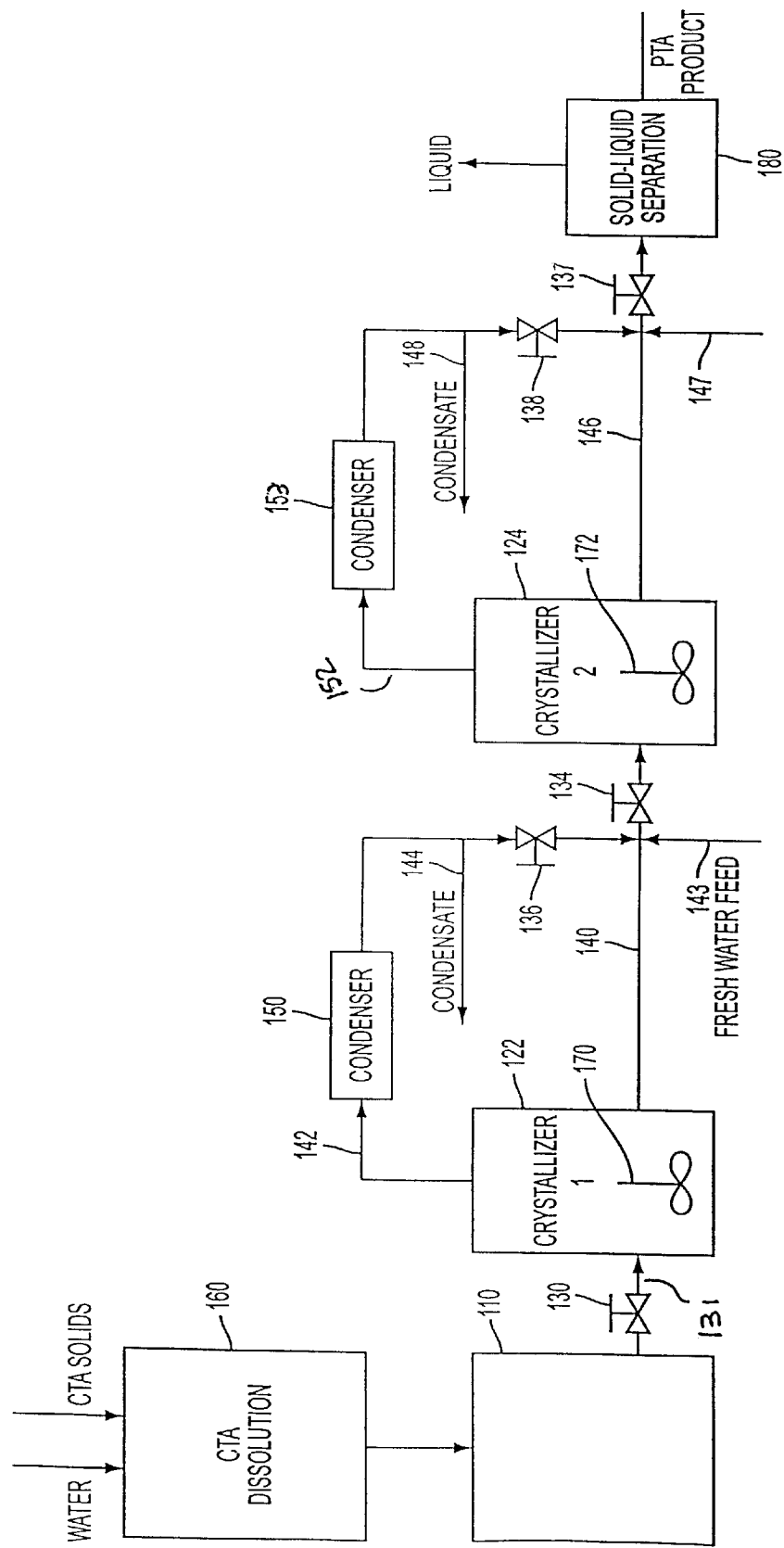

Crude aromatic dicarboxylic acids such as TPA may be prepared by a variety of known oxidation processes. For example, p-xylene may be contacted with oxygen or an oxygen-containing gas in the presence of an oxidation catalyst and an aliphatic carboxylic acid solvent in a first reactor. Catalytic oxidation of the p-xylene in the first reactor occurs at a first temperature to produce an intermediate product. The intermediate product is fed to a second reactor wherein the first reactor product is contacted with oxygen which is fed to the second reactor at a second volumetric flow rate equal to 3% or less of the first reactor volumetric flow rate. The intermediate product is digested in the second reactor to produce a refined product. Alternatively, TPA may be produced in a recirculating flow reactor wherein p-xylene is contacted with oxygen in the presence of a solvent and oxidation catalyst. According to this alternative process, a gas containing at least 50% oxygen is introduced into the recirculating flow reactor. The reactor is maintained at a temperature of from 100 to 200° C. and a pressure of from 6.9 to 13.8 bars gauge—barg (100 to 200 pounds per square inch—psig). The contents are maintained within the reactor for a residence time of from 30 to about 90 minutes. Another process for the preparation of crude TPA comprises the oxidation of a 30:1 solvent:p-xylene mixture within a continuous plug flow reaction zone, which is formed by a plurality of plug flow reactors, a plurality of continuously stirred tank reactors or combination of the two. The inlet temperature of the continuous plug flow reaction zone is less than the outlet temperature thereof.

The crude terephthalic acid (CTA) solid produced, for example, by the oxidation pf p-xylene is recovered from the oxidation process by conventional solid-liquid separation techniques. The CTA typically contains impurities such as 4-CBA, fluorenones and p-toluic acid. For example, the combined total concentration of 4-CBA and p-toluic acid in the CTA solids typically is about 150 to 1,100 ppmw, more typically about 150 to 900 ppmw, and still more typically 150 to 500 ppmw.

The purification of the CTA comprises hydrogenating the CTA to convert CBA to p-toluic acid and the color bodies, or precursors of color bodies, to colorless compounds. A solution of the CTA to provide a concentration of about 10 to 35 weight percent CTA solids, preferably about 25 to 35 weight percent CTA in a solvent such as acetic acid or, preferably, water. The CTA solution is formed by heating the solvent or slurry of CTA to a temperature that is sufficient to dissolve the CTA at the concentration desired, e.g., temperatures in the range of about 260 to 320° C. Solution temperatures in the range of about 260 to 320° C. using a solvent such as water require that the solution be maintained at an elevated pressure, e.g., a pressure in the range of about 46.9 to 113 bars absolute—bara (680–1640 pounds per square inch absolute (psia).

The CTA solution is subjected to liquid phase hydrogenation by contacting the liquid solution with hydrogen in the presence of a hydrogenation catalyst, e.g., a noble Group VIII metal on a catalyst support material to cause certain of the impurities to be hydrogenated to other compounds. For crude TPA, fluorenones and 4-CBA are converted to fluorenes and p-toluic acid, respectively. Assuming that there is substantially complete conversion of 4-CBA to p-toluic acid and assuming that the CTA solution fed to the hydrogenation reactor has a combined total concentration of 4-CBA and p-toluic acid of 150 to 1,100 ppmw, then the concentration of p-toluic acid alone in the product stream from the hydrogenation reactor 110 is 150 to 1,100 ppmw, based on the TPA present. Similarly, if the combined total concentration of 4-CBA and p-toluic acid in the solution fed to the hydrogenation reactor is 150 to 900 ppmw or 150 to 500 ppmw, and substantially complete 4-CBA conversion is assumed, the p-toluic acid concentration in the product stream from the hydrogenation reactor is 150 to 900 ppmw or 150 to 500 ppmw, respectively.

The temperature of the hydrogenation product stream typically is in the range of about 260 to 320° C. The hydrogenation product stream is fed to a crystallization zone comprising a plurality or sequence of series-connected crystallizer stages that together operate to reduce the temperature of the post-hydrogenation stream to a lower temperature, typically about 75 to 150° C., more typically about 90 to 110° C. The reduction in temperature is accompanied by a concurrent precipitation of TPA from solution in the form of a white crystalline solid. The crystalline TPA in the final stage of crystallization is separated from the solvent using conventional a solid-liquid separation device such as a centrifuge or rotary vacuum filter. The crystallization zone may comprise two to eight, preferably three to six, most preferably four or five, crystallizers or crystallizer stages, The numbers of crystallizer stages employed in the process may affect the quality of the final product. The correct staging of the temperatures of the sequence of series-connected crystallizer stages will increase the purity of the final product with respect to p-toluic acid.

The plurality of crystallizer stages includes a first and a last crystallizer stage. The temperature within the first crystallizer stage normally is in the range of about 200 to 260° C. and the temperature within the last crystallizer stage normally is in the range of about 80 to 100° C. The operating temperatures of the crystallizer stages may become successively lower from the first to the last crystallizer stage. The last crystallizer stage produces a product slurry, which contains on a solid basis less than 25 ppm 4-CBA and less than 150 ppmw p-toluic acid. In accordance with the present invention, an aromatic dicarboxylic acid such as TPA is crystallized in a first crystallizer stage by cooling the hydrogenation feed stream by controlled rate evaporative cooling (or flashing) by a reduction of the pressure (as compared to the feed stream pressure) within the first crystallizer or crystallizer stage. Solvent removed as a vapor from the crystallizer is condensed and some or all of the condensed solvent is returned to the crystallization zone at a point downstream from the crystallizer from which the solvent vapor was removed. Additional aromatic dicarboxylic acid is crystallized in a second crystallizer stage at a second temperature, less than the first temperature, while allowing solvent evaporation. Solvent, either condensed from solvent vapor produced in the preceding crystallizer and/or fresh solvent, may be added to the second crystallizer stage.

Each of the plurality of crystallizer stages has a mass flow rate of material entering and exiting the crystallizer stage. The mass flow rate of material entering the first crystallizer stage may equal 0.7 to 1.3 times the mass flow rate of material exiting the last crystallizer stage. Preferably, the mass flow rate of material entering the first crystallizer stage is substantially equal to the mass flow rate of material exiting the last crystallizer stage.

Each crystallizer stage of the process of our invention has a plurality of operational similarities comprising the following main elements:

1. A crystallization unit or vessel (crystallizer) equipped with agitation means such as one or more impellers;
2. A feed line to the crystallizer;
3. A product removal line from the crystallizer;
4. A solvent distillate or vapor removal line from the crystallizer leading to a condenser wherein some or all of the solvent vapor is condensed; and
5. A solvent feed line to a downstream point or portion of the crystallization zone for feeding the liquid condensed in the condenser.

The crystallization unit is a well-mixed constant volume vessel containing a slurry of TPA crystals. The solvent typically is water saturated with TPA at the operating temperature of the crystallizer. Other solvents, such as acetic acid, can also be used. The operating temperature of each crystallization unit in combination with the temperature and concentration of the feed stream determines how much TPA will crystallize in each stage. To crystallize a larger portion of the TPA, the temperature must be lowered to a point where the solubility of TPA in the solvent, e.g., water, is reduced to allow more TPA to crystallize. Independent control of the pressure determines the operating temperature of the crystallization units. Pressure control can be accomplished by regulating the back-pressure in the crystallization units using, for example, but not limited to a valve in the distillate line.

As a result of reduced pressure (relative to the pressure of the feed stream to the crystallization unit), solvent evaporates and is removed from the crystallization unit as a vapor, thus concentrating the solution. A portion of the TPA precipitate crystallizes on crystals already existing in the vessel, and a portion of the TPA nucleates as separate new crystals. The amount of TPA that is transformed from the liquid phase to the solid phase is a function of the operating temperature (controlled by pressure reduction) of the crystallizer and the TPA equilibrium concentration at that temperature.

Normally, the feed to the first crystallizer is fed below the surface of the slurry contained therein toward the bottom of the vessel where the hydrostatic head is higher. The increased pressure at this point in the crystallization unit and the surrounding liquid prevent excessive flashing. Agitation devices such as impellers are provided in the crystallization units. When the hydrogenation reactor product stream is introduced to the first crystallization unit at a zone of sufficient mixing, local high super-saturation, which promotes the formation of small (or fine) crystals, can be minimized.

A product stream is continuously withdrawn from each crystallization unit. The product stream preferably is removed from a well-mixed zone of the crystallization unit such that the contents of the product stream represent an average of the overall contents within each crystallization unit. The product stream is fed to a successive or subsequent crystallizer stage operated at a lower temperature, preferably to a well-mixed zone of the next crystallization unit. Because each successive crystallization unit operates at a lower temperature, a portion of the TPA remaining in solution crystallizes, which portion is determined by the equilibrium TPA concentration at the operating temperature of the second crystallization unit 124.

As mentioned above, solvent distillate or vapor is continuously removed from the first and subsequent crystallizer stages and transported to a condenser to cool and condense the vapor. Either a portion or all of the distillate may be condensed at this point. In addition, a sub-cooling of the vapor to a temperature substantially below the boiling point can also be accomplished within the condenser. All or a portion of the condensed solvent is recycled to the crystallization zone at a point downstream from the crystallizer from which the solvent was removed as a vapor. Preferably, the condensed solvent is recycled to the crystallization zone by feeding the condensed solvent to the product removal line of the crystallizer from which the solvent was removed as a vapor. Any condensed solvent not returned or recycled to the crystallization zone may be utilized elsewhere in the TPA purification system, e.g., in preparing the CTA solution feed to the hydrogenation reactor. The final crystallization unit acts as a hold-up vessel for the slurry, retaining the slurry before a solid-liquid separation step. The second and subsequent crystallizers operate in a manner similar to that of the first crystallizer stage.

Condensed solvent from an upstream crystallizer stage may be recycled to an immediately downstream crystallizer stage or recycled to a crystallizer stage other than an immediately downstream crystallizer stage. Both condensed solvent and fresh solvent may be supplied to one of the subsequent crystallizer stages.

The product stream from any or all of the crystallizer stages may be diluted using a dilution liquid such as water at a temperature which is the same as, or substantially the same as, the operating temperature of the crystallizer stage from which the product stream was removed. The addition of the dilution liquid to the product stream has the effect of reducing the overall concentration of TPA and any impurities present in the product stream. If no dilution liquid is added to the product stream from each crystallizer, the overall concentration of TPA in each product stream continues to rise. In crystallization processes in which dilution liquid is not recycled, the product stream from the hydrogenation reactor is thus at such a dilution that the process will yield a pre-determined solid TPA concentration hold-up after the final crystallizer stage. That is, by knowing the amount of liquid added and removed and by knowing the amount of TPA crystallizing, the solid TPA concentration hold up can be determined. By the addition of dilution liquid (perhaps water) to the product stream from each crystallizer stage, the dilution required in the initial feed stream is much lower.

The dilution liquid added to the product stream can originate from a number of sources. Firstly, the condensate from the crystallizer stage from which the product is withdrawn may be condensed and partially or wholly recycled back to the product stream from that stage. Secondly, a fresh solvent, e.g., water, supply can be used, in an amount that is greater than, less than or equal to the amount of liquid removed in the form of distillate. Thirdly, if more than one crystallizer stage is being used, condensate from a stage other than the immediately preceding stage may be recycled to the crystallizer stage of interest. This condensate normally is heated to the same temperature as the operating temperature of the preceding crystallizer stage.

In each case, either a portion or all of the condensed solvent is recycled to the product feed supplying the crystallizer stages or additional solvent is supplied to the crystallizer stages or a combination of the two may be used. If more than two crystallizer stages are provided, the percentage of solvent supplied to each crystallizer stage may be varied. For example, some crystallizer stages may be supplied with an amount of solvent equal to the amount evaporated in the preceding stage, and some of the crystallizer stages may be supplied with no solvent.

The addition point for the dilution liquid back into the system may be at some point in the transfer line between crystallizers. This line normally contains a valve to control the flow rate of product from one crystallizer stage to the next. The residence time for a crystallizer stage is given by the volume of the crystallizer stage divided by the product slurry volumetric flow rate from the crystallizer stage. As an alternative to transfer line/feed line addition, the dilution liquid may be added directly to the crystallization unit. In this case, the dilution liquid preferably is added below the surface of the liquid, most preferably at the base of the crystallization unit, in a well mixed zone.

When all of the distillate from each crystallization unit is recycled to the product stream from that crystallization unit, the TPA concentrations entering the crystallizer stages will be equal to each other irrespective of whether the TPA is in the liquid phase or the solid phase. Thus, the original feed stream liquid TPA concentration will be approximately equivalent to the final product solids hold-up concentration given that only a minor portion of TPA will remain in solution and not crystallize.

Compared to sequential TPA crystallization processes wherein there is no downstream recycle of condensed solvent, the stream from the hydrogenation reactor to the first crystallization unit may be more concentrated and have a reduced flow rate. Likewise, a reduction of feed flow rates from one crystallizer stage to the next results in a reduction in product flow rates. To maintain a pre-defined residence time with reduced feed flow rates, the volume of the crystallization units must be reduced. With a substantially constant flow rate, for example, the upstream, higher temperature and downstream, lower temperature crystallizer stages can have a substantially equal volume yet still have the same residence time.

In general, the strategy for selecting the temperature profile for a number of crystallizer stages has been to select the temperatures which crystallize smaller portions of TPA in each stage than the stage before. It has been established that this technique will not only crystallize less TPA in each downstream stage but it will also minimize contamination of the product by p-toluic acid. The ideal case where this mechanism would be taken greatest advantage of is in a series of infinite crystallizer stages, approximating batchwise conditions. The limit of practical operation does not allow for this. In the current invention, the higher TPA concentration in the original feed stream enhances this mechanism, as higher TPA concentrations cause more of the TPA to crystallize at higher temperatures (in the upstream stages).

The product removal line from the final crystallizer feeds a conventional solid-liquid separation apparatus for the recovery of the crystalline TPA product containing less than about 150 ppmw p-toluic acid. Since the temperature of the last crystallizer stage may be less than the normal boiling point for the solvent, a vacuum filter (instead of a pressure filter) may be used. The wet crystalline TPA may be washed before being discharged to a dryer. The filtered mother liquor and the fluid used for washing are collected for recycle to the hydrogenation step. A portion of the filtrate liquid may be purged to reduce the build-up of impurities in the system.

Referring to the accompanying FIG. 1, a solvent such as water and solid crude terephthalic acid (CTA) are fed to are fed to a CTA dissolution vessel 160. In the dissolution vessel 160, the CTA solids are diluted with a solvent such as water, to a concentration of about 10 to 35 weight percent CTA solids, more typically about 25–35 weight percent CTA solids. The diluted CTA solids are brought to a temperature, e.g., 260° C. to 320° C., which is sufficient to dissolve all of the CTA solids. At the elevated temperature and pressure, the CTA solids are driven into solution. The solution of CTA is fed, along with hydrogen, to hydrogenation reactor 110 wherein impurities present are hydrogenated in the liquid phase. Hydrogenation reactor 110 contains one or more beds of a conventional hydrogenation catalyst such as a nobel Group VIII metal on a catalyst support material. The hydrogenation product is removed from hydrogenation reactor 110 and fed via valve 130 to first crystallization unit 122 at a point below the surface of the slurry contained in vessel 122, near the bottom of vessel 122, where the hydrostatic head is higher. An agitation device such as impeller 170 is provided in first crystallization unit 122 and other crystallization units as well.

A product stream is continuously removed from first crystallization unit 122 via conduit 140. The product stream is removed from a well-mixed zone of the crystallization unit 122 such that the contents of the product stream represent an average of the overall contents within that crystallization unit 122. The product stream is fed via a valve 134 to a second, successive crystallizer vessel 124 which is operated at a pressure and temperature lower than the pressure and temperature within crystallizer 122. The product stream is fed to a well-mixed zone of crystallization unit 124. Because the successive crystallization unit 124 operates at a lower temperature, a portion of the TPA remaining in solution crystallizes, which portion is determined by the equilibrium TPA concentration at the operating temperature of the second crystallization unit 124.

Solvent vapor is removed continuously from first crystallizer stage 122 via conduit 142 and fed to condenser heat exchanger 150 to cool wherein all or a portion of the solvent is condensed. Sub-cooling of the vapor to a temperature significantly below the boiling point also can be accomplished with the heat exchanger. A portion or all of the condensed solvent is fed to product stream 140 through a valve 136. Any condensed solvent not recycled to the product stream may be removed through conduit 144. Second crystallizer stage vessel 124 operates in a manner similar to that of first crystallizer stage 110 and includes crystallization unit 124 having impeller 172 therein. Product is removed from crystallization unit 124 via conduit 146. Solvent vapor is removed from second crystallization unit 124 and sent to condenser 152 wherein solvent vapor is condensed and the condensed solvent is recycled via valve 138 and/or eliminated via conduit 148. Fresh, additional solvent, e.g., water, may be added to the sequential crystallization system depicted in FIG. 1 via line 143 and/or line 147.

The crystallization product is removed from crystallizer 124 via conduit 146 and transferred via valve 137 to solid-liquid separation zone 180. The temperature at the last crystallizer stage may be less than the normal boiling point for the solvent which permits solid-liquid separation to be a vacuum filter. The solid-liquid separation 180 removes mother liquor from a crystalline cake in a first zone. The crystalline cake then is washed in the second zone.

EXAMPLES

The novel crystallization process of the present invention is further illustrated by the following examples.

Comparative Example

The data reported in Table 1 for this Comparative Example were taken from Example 8 of U.S. Pat. No. 3,931,305. Sequential evaporative cooling was performed in each of six crystallizer stages without any recycle of solvent evaporated from each crystallizer stage. In Table 1 Sample Location refers to the point in the sequential crystallization system where temperature was measured and a sample was taken to measure the weight percent solid TPA present, Stage refers to a crystallizer stage in the sequence of 6 crystallizer stages, Stage 1-Stage 2 indicated that a smape was taken from the product stream between the first and second crystallizers, Temp refers to temperature in ° C., and TPA Solids refers to the total weight percent, based on the total TPA fed to crystallizer stage 1, TPA solids.

In Example 8 of U.S. Pat. No. 3,931,305, the feed to the first crystallizer stage contains 18 weight percent dissolved TPA. With solvent evaporation (evaporative cooling) and no recycle, the TPA becomes more concentrated as it proceeds through the crystallizer stages. After the last crystallizer stage, the total concentration of TPA (sum of liquid and solid concentrations) approximately equals the solids hold-up in the product stream. That is, substantially all of the TPA, which was fed to the first stage as a liquid, is converted to a solid, and the solid is substantially free from other components. With availability of the solubility curve of TPA and water, a simulation was performed to determine the solids hold-up in the product stream. The simulation was performed knowing the temperature of each crystallizer stage and knowing the amount of TPA crystallized. The simulation shows a solids hold-up in the product stream from the final crystallizer of 31.40%.

TABLE 1

| Sample Location | Comparative Example | | Example 1 | | Example 2 | |
|---|---|---|---|---|---|---|
| | Temp | TPA Solids | Temp | TPA Solids | Temp | TPA Solids |
| Stage 1 feed | 276.67 | 0 | 276.67 | 0 | 276.67 | 0 |
| Stage 1– Stage 2 | 251.67 | 42.08 | 251.67 | 71.76 | 265.20 | 42.08 |
| Stage 2– Stage 3 | 204.44 | 93.28 | 204.44 | 95.98 | 218.25 | 93.32 |
| Stage 3– Stage 4 | 165.56 | 98.69 | 165.56 | 99.02 | 175.07 | 98.62 |
| Stage 4– Stage 5 | 135.00 | 99.63 | 135.00 | 99.68 | 139.44 | 99.63 |
| Stage 5– Stage 6 | 121.11 | 99.79 | 121.11 | 99.80 | 123.33 | 99.79 |
| Stage 6 Product | 100.00 | 99.91 | 100.00 | 99.91 | 100.00 | 99.91 |

Example 1

The Temp and TPA Solids columns listed under Example 1 in Table 1 show the TPA solids resulting when the same operating temperatures are assumed for each crystallizer but 100% of the condensate is recycled to the system at the feed point to the next crystallizer. The same solids hold-up time in each crystallizer was achieved by increasing the solids concentration to 30% in the feed stream to the first crystallizer and by decreasing the size of the upstream crystallizers. The same production rates were obtained by decreasing the overall flow rate to the first crystallizer stage. In this example 71.76% of the TPA crystallized in the first stage as opposed to 42.08% in the Comparative Example. By the second stage 95.98% had crystallized in comparison to 93.28% in the Comparative Example. Example 1 shows more TPA can be crystallized at a given temperature using 100% solvent recycle.

Example 2

The Temp and TPA Solids columns listed under Example 2 in Table 1 report data for a process that is conditioned to yield the same amount of crystallized TPA (per crystallizer stage) as was obtained in the Comparative Example. As with Example 1, 100% of the condensed solvent is recycled. The results show that 42.08% of the TPA can be crystallized in the first stage even if the temperature in the first stage is maintained higher, 264.1° C. as opposed to 251.7° C. as in the Comparative Example. At higher temperatures, the mixtures are further from the p-toluic acid solubility curve. Therefore, there is less p-toluic acid co-crystallization at higher temperatures. It is expected that the crystals produced at 264.1° C. would be purer than the crystals produced at 251.67° C. Example 2 shows that the purity may be increased, without reducing the quantity of the product.

The invention has been described in detail with particular reference to preferred embodiments thereof, but it will be understood that variations and modifications can be effected within the spirit and scope of the invention.

We claim:

1. Process for the recovery of crystalline terephthalic acid containing less than about 150 parts per million by weight (ppmw) p-toluic acid, based on the weight of the terephthalic acid, by the steps comprising:
   (1) providing a solution containing about 10 to 35 weight percent dissolved terephthalic acid having dissolved therein about 150 to 1100 ppmw p-toluic acid, based on the weight of the terephthalic acid present, and having a temperature of about 260 to 320° C. at a pressure sufficient to maintain the solvent in the liquid phase;
   (2) feeding the solution of step (1) to a crystallization zone comprising a plurality of series-connected crystallizers wherein the solution is subjected to rate-controlled evaporative cooling by sequential reduction in pressure and temperature to cause crystallization of terephthalic acid, wherein the pressure of the solution at the end of the crystallization zone is about ambient pressure or less;
   (3) condensing solvent evaporated from the crystallizers and returning the condensed solvent to the crystallization zone at a point subsequent to the crystallizer from which it was obtained; and
   (4) recovering solid, crystalline terephthalic acid containing less than about 150 parts ppmw p-toluic acid, based on the weight of the terephthalic acid, by liquid-solid separation at ambient pressure.

2. Process according to claim 1 wherein the solution of step (1) contains about 25 to 35 weight percent dissolved terephthalic acid having dissolved therein about 150 to 900 ppmw p-toluic acid, based on the weight of the terephthalic acid present and the plurality of series-connected crystallizers consists of two to eight crystallizers.

3. Process according to claim 2 wherein the temperature of the first crystallizer is in the range of about 260 to 320° C. and the temperature of the last crystallizer is in the range of about 90 to 110° C. and the plurality of series-connected crystallizers consists of three to six crystallizers.

4. Process for the recovery of crystalline terephtalic acid containing less than about 150 parts per million per weight (ppmw) p-toluic acid, based on the weight of terephthalic acid, comprising:
   (1) feeding a solution comprising a solvent, about 10–35 weight percent dissolved terephthalic acid, and 150–1,100 ppmw p-toluic based on the weight of the terephthalic acid present, to a crystallization zone comprising a plurality of series-connected crystallizers wherein solvent is removed as a vapor from one or more crystallizers;
   (2) condensing the solvent evaporated from at least one of said crystallizers, and returning the condensed solvent to a crystallizer located down-stream in the series to the crystallizer from which it was obtained; and
   (3) recovering terephthalic acid containing less than about 150 ppmw p-toluic acid, based on the weight of the terephthalic acid.

5. Process according to claim 4, wherein first crystallizer is operated at a temperature of about 260 to 320° C. and the temperature of the last crystallizer is in the range of 90 to 110° C. and the plurality of series connected crystallizers consists of 2–8 crystallizers.

6. Process according to claim 4, wherein solvent is removed from each of the crystallizers.

7. Process according to claim 4, wherein each crystallizer has a product removal line, and said condensed solvent is fed to the product removal line of the crystallizer from which the solvent was removed as a vapor.

8. Process of claim 4, wherein each crystallizer has a product removal line, through which is fed a product stream from the crystallizer to which the product removal line is attached, further, wherein said product stream may be diluted with a diluent other than said condensed solvent.

9. Process according to claim 4, further comprising recovering solid, crystalline terephthalic acid containing less than about 150 ppmw p-toluic acid at ambient pressure.

* * * * *